United States Patent [19]
Farr et al.

[11] Patent Number: 5,226,887
[45] Date of Patent: Jul. 13, 1993

[54] COLLAPSIBLE FOLDING ANGIOPLASTY BALLOON

[75] Inventors: Andrew F. Farr, Spring Valley; Herbert R. Radisch, Jr., San Diego, both of Calif.

[73] Assignee: InterVentional Technologies, Inc., San Diego, Calif.

[21] Appl. No.: 832,366

[22] Filed: Feb. 7, 1992

[51] Int. Cl.⁵ ............................................. A61M 29/00
[52] U.S. Cl. ........................................ 604/96; 606/194
[58] Field of Search .................................. 604/96–103; 606/191–194

[56] References Cited

U.S. PATENT DOCUMENTS

| | | | |
|---|---|---|---|
| 4,140,126 | 2/1979 | Choudhury | 128/325 |
| 4,141,364 | 2/1979 | Schultze | 128/349 |
| 4,292,974 | 10/1981 | Fogarty et al. | 128/344 |
| 4,406,656 | 9/1983 | Hattler et al. | 604/280 |
| 4,608,984 | 9/1986 | Fogarty | 128/344 |
| 4,627,436 | 12/1986 | Leckrone | 128/303.1 |
| 4,685,458 | 8/1987 | Leckrone | 128/303.1 |
| 4,686,982 | 8/1987 | Nash | 128/305 |
| 4,705,517 | 11/1987 | DiPisa, Jr. | 623/12 |
| 4,787,388 | 11/1988 | Hofmann | 128/344 |
| 4,896,669 | 1/1990 | Bhate et al. | 606/194 |
| 5,015,231 | 5/1991 | Keith et al. | 604/96 |
| 5,042,985 | 8/1991 | Elliott et al. | 606/192 |
| 5,108,415 | 4/1992 | Pinchuk et al. | 604/96 |

Primary Examiner—John D. Yasko
Attorney, Agent, or Firm—Nydegger & Associates

[57] ABSTRACT

An inflatable angioplasty balloon is formed in an unstressed configuration for inflation into an expanded configuration and deflation into a collapsed configuration. The balloon has a body portion and two hollow end portions, with the end portions being attached to opposite ends of the body portion.

In the balloon's unstressed configuration, the body portion has three flat folding regions extending the length of the body portion. Successive folding regions are separated from each other by curved reinforcing regions. The end portions are configured and oriented to guide the folding regions of the balloon into a pleated, collapsed configuration when the interior of the balloon is evacuated.

16 Claims, 2 Drawing Sheets

COLLAPSIBLE FOLDING ANGIOPLASTY BALLOON

FIELD OF THE INVENTION

The present invention pertains generally to devices for enlarging the lumen of a restricted blood vessel. More particularly, the present invention pertains to angioplasty devices which relieve stenoses that form in a blood vessel. The present invention particularly, though not exclusively, pertains to inflatable angioplasty balloons which can be predictably collapsed into a small cross-section configuration.

BACKGROUND OF THE INVENTION

A large number of balloon angioplasty devices exist for relieving arterial stenoses by compression of the stenosis. Balloon angioplasty devices afford numerous advantages over alternative methods and apparatus which can be used for removing stenoses that are formed when plaque builds up in a patient's arteries. Foremost among these advantages is that open heart bypass surgery can often be avoided by using angioplasty surgical techniques to relieve stenoses in arteries which supply the heart. It is preferable to avoid open heart bypass surgery when possible because such surgery, as is well known, is relatively invasive and entails a relatively long post-operative recovery period. Accordingly, it is preferable to use relatively simpler angioplasty surgical procedures when such procedures are feasible. In angioplasty surgery, an inflatable balloon which is initially in a collapsed configuration is attached to a catheter, and the catheter is connected to a source of fluid. The balloon is then positioned at the desired location in the affected artery by inserting the balloon through an appropriate major artery, e.g. the femoral or carotid artery, until the balloon has been positioned next to the stenosis to be treated. Once the balloon has been properly positioned, fluid is infused into the balloon through the catheter to inflate and expand the balloon within the artery. As the balloon expands, it dilates the lumen of the artery and compresses the stenosis. Upon being compressed, the stenosis may break up or flatten out against the arterial wall. The balloon is subsequently deflated and, once in its collapsed configuration, it is either withdrawn from the artery or placed across another stenosis, to restore normal blood flow through the artery.

To effectively expand the lumen and compress the stenosis, it is desirable that the balloon be reliably inflatable to a relatively large diameter when the balloon is infused with fluid. This is so in order to evenly expand the balloon within the affected artery to evenly dilate the vessel, compress and hence compromise the stenosis. Also, it is desirable that the balloon be reliably collapsible to a minimal, radially compact cross sectional shape incident to balloon insertion and withdrawal. This is to facilitate insertion and withdrawal of the balloon in artery. While existing angioplasty balloons are collapsible, it is unfortunately the case that many existing balloons typically cannot be reliably collapsed, i.e., deflated, to a radially compact minimal cross section after inflation. Instead, they often flatten when deflated. This flattening increases interference between the flattened balloon and the arterial wall during balloon withdrawal or when being placed across a second stenosis. Consequently, a flattened balloon can be relatively difficult to withdraw from an artery.

Existing devices attempt to provide symmetrically collapsible structures by a variety of methods. For example, a venous catheter is disclosed in U.S. Pat. No. 4,406,656 to Hattler, et al. which has multiple collapsible lumens that are intended to collapse around a central non-collapsible lumen. For the Hattler, et al. device, the central lumen retains its shape when the catheter is collapsed. Additionally, a dilatation catheter is disclosed in U.S. Pat. No. 4,896,669 to Bhate, et al., which has a crimped outer tubular balloon portion and an inner catheter extending lengthwise through the crimped outer balloon portion. With this combination, the Bhate, et al. device attempts to provide a balloon that collapses to a small cross section by crimping portions of the outer balloon to guide the non-crimped portion of the outer balloon around the inner catheter when the balloon is collapsed.

The Hattler, et al. device is not intended for use in angioplasty procedures and devices such as Bhate, et al. have scored, interconnected, crimped, or pre-folded portions of the balloon that are weakened relative to other portions of balloon. Scored or crimped devices are, unfortunately, susceptible to leaking or tearing when the balloon is inflated at the relatively high inflation pressures (upwards of four atmospheres) that are typically used in angioplasty procedures. Also, such devices do not always provide a balloon which can be reliably collapsed to a small, compact cross sectional shape. Instead, the balloons may occasionally flatten when deflated. The present invention recognizes that it is possible to provide an angioplasty balloon which reliably collapsed into a minimal, compact cross section without weakening portions of the balloon.

Accordingly, it is an object of the present invention to provide a collapsible angioplasty balloon which can be reliably collapsed into a compact minimal cross sectional configuration. Another object of the present invention is to provide a collapsible angioplasty balloon that can be reliably inflated into a radially-symmetrical, relatively large cross sectional configuration. It is also an object of the present invention to provide a collapsible angioplasty balloon all of the portions of which have a substantially high resistance to leaking and tearing when the balloon is inflated. A further object of the present invention to provide a collapsible angioplasty balloon which is relatively easy to use and comparatively cost-effective to manufacture.

SUMMARY OF THE INVENTION

In overview, the angioplasty balloon of the present invention has a hollow body that is changeable between three identifiable configurations. These configurations are an inflated configuration, wherein the interior of the body is pressurized with fluid to expand the body against an arterial stenosis, a collapsed configuration, wherein the interior of the body is evacuated to pleat the sidewalls of the balloon and deflate the balloon, and an unstressed configuration which is intermediate the inflated and the collapsed configuration. In accordance with the present invention, the body is formed with a predetermined number of regions which are longitudinally oriented on the body parallel to the axis of the body. The ends of the body are each attached to a tapered end portion which is configured and oriented to guide the regions of the body and collapse the body into a compact, minimal cross-sectional shape when the balloon is deflated.

More particularly, the inflatable angioplasty balloon of the present invention has a hollow tubular body portion which has first and second ends. A plurality of folding regions are formed longitudinally on the body, and each of the folding regions extends from the first end of the body to the second end. A reinforcing region is positioned between successive folding regions. Like the folding regions, the reinforcing regions extend longitudinally from the first end of the body to the second end. Importantly, when the body is in an unstressed configuration, i.e., when the balloon is not inflated or collapsed, each of the folding regions has a radius of curvature which is greater than the radius of curvature of each of the reinforcing regions. In the preferred embodiment, each folding region is essentially flat and each reinforcing region is curved when the balloon is in the unstressed configuration. Consequently, the reinforcing regions are stiffer than the folding regions.

Additionally, a first hollow end portion is coaxially oriented on the body and extends longitudinally from the first end of the body portion. Likewise, a second hollow end portion is coaxially to and longitudinally extends from the second end of the body portion. Each of the end portions are tapered and each has a widened base end which is attached to the body portion, and a narrower open base end which is distanced from the body portion.

Importantly, each of the tapered end portions has a plurality of longitudinally extending connecting regions which are separated by guiding regions. When the balloon is in an unstressed configuration, each of the connecting regions of the tapered portion has a greater radius of curvature than does each of the guiding regions. Accordingly, the connecting regions of the tapered portions are less stiff than are the guiding regions.

To guide the body of the balloon into a compact, minimized cross-sectional configuration when the balloon is collapsed, the tapered portions are integrally formed with the body portion in a predetermined orientation. More specifically, each of the connecting regions of each tapered portion extends longitudinally from a reinforcing region of the body portion. On the other hand, each of the guiding regions extends longitudinally from a respective folding region of the body. Consequently, when the balloon is deflated, the relatively stiff guiding regions of the tapered portions guide the relatively less stiff folding regions of the body portion into a collapsed configuration which is characterized by a pleated, radially compact cross-sectional shape. In contrast, when the balloon is in its inflated configuration, the body portion and the tapered portions of the balloon have substantially circular cross sectional shapes.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
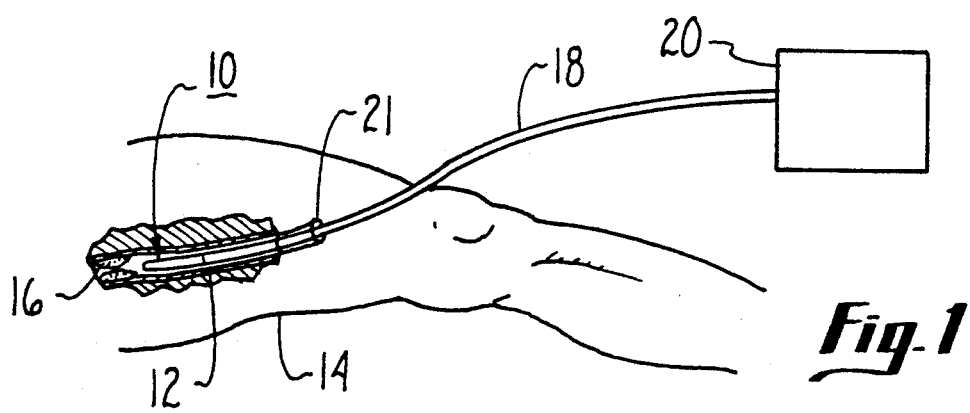
FIG. 1 is a perspective view of the novel collapsible angioplasty balloon of the present invention, shown in its intended environment with balloon in its collapsed configuration.

Referring initially to FIG. 1, an angioplasty balloon is shown and generally designated 10. As shown, balloon 10 is insertable into an artery 12 of a patient 14 for the purpose of relieving an arterial plaque stenosis 16. To this end, FIG. 1 shows that balloon 10 is connected in fluid communication to a hollow catheter 18, and catheter 18 is in turn connected to a source 20 of fluid for infusing fluid into balloon 10 to expand balloon 10 against stenosis 16. If required, balloon 10 with catheter 18 can be inserted into patient 14 through an insertion catheter 21. Balloon 10 is made of any suitable angioplasty balloon material, such as polyethylene terephthalate or polyetherimid.

Figure 2:
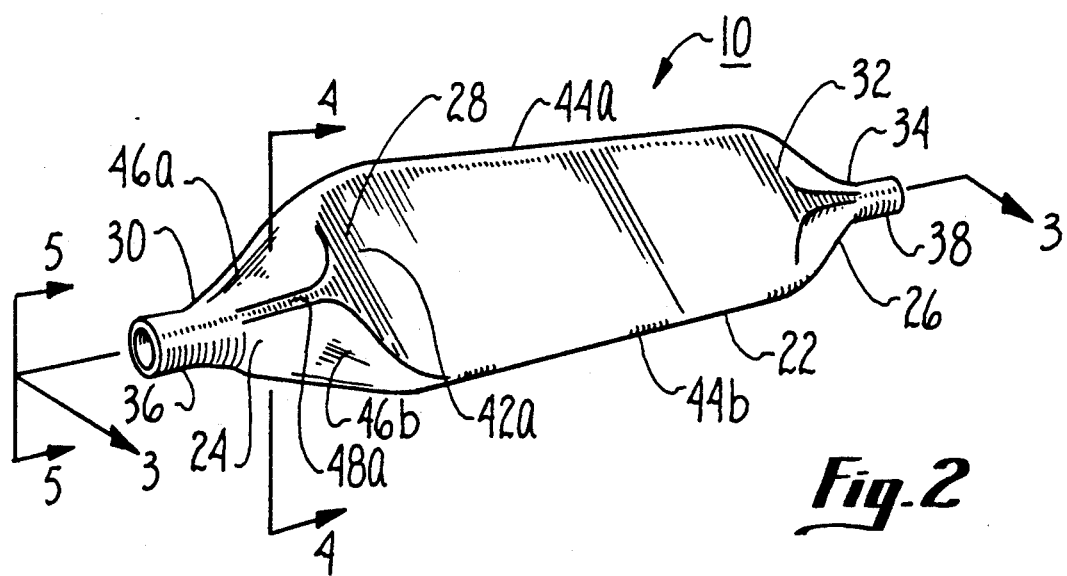
FIG. 2 is a perspective view of the balloon of the present invention shown in FIG. 1, with the balloon in its unstressed configuration.
Figure 3:
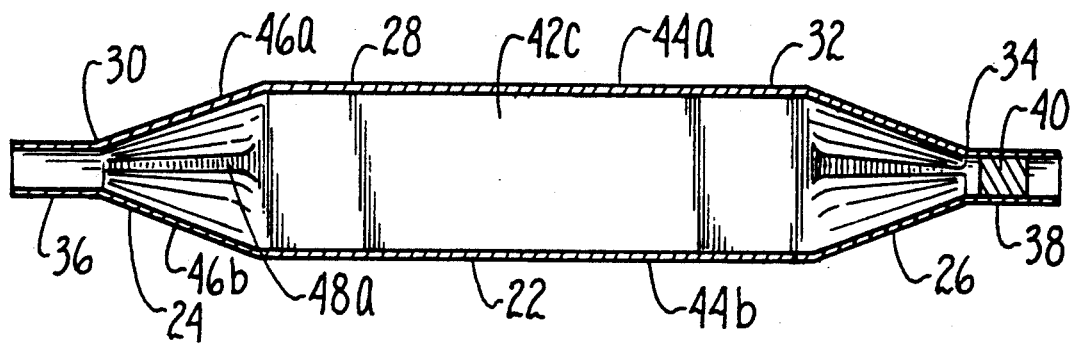
FIG. 3 is a cross-sectional view of the balloon as seen along the line 3—3 in FIG. 2.

Now referring to FIGS. 2 and 3, balloon 10 is shown in its unstressed configuration, i.e. the configuration balloon 10 has when the fluid pressure inside balloon 10 is substantially equal to the fluid pressure of the environment which surrounds the exterior of balloon 10. As shown in FIGS. 2 and 3, balloon 10 has a hollow body portion 22 and two hollow end portions 24, 26, which are joined in fluid communication to body portion 22. As shown in FIG. 2, each of the end portions 24, 26, is tapered inwardly. More particularly, end portion 24 converges from a widened base end 28 to a narrower open base end 30. Similarly, end portion 26 converges from a widened base end 32 to a narrower open end 34. The open ends 30, 34 are joined in fluid communication with hollow cylindrical tube portions 36, 38 which, in turn, can be attached to a catheter 18, hollow guide wire, or other appropriate angioplasty surgery component. Alternatively, tube portion 38 can have a plug 40 positioned therein to block the lumen of tube portion 38.

Importantly, the material of balloon 10 is a non-toxic, chemically inert, yet strong material which is suitable for angioplasty surgery applications. In particular, the material of balloon 10 should be a high tensile strength material which can withstand tensile forces of greater than twelve thousand (12,000) psi. Preferably, body portion 22, tapered portions 24, 26, and tube portions 36, 38 are integrally formed from a single piece of material.

Figure 4A:
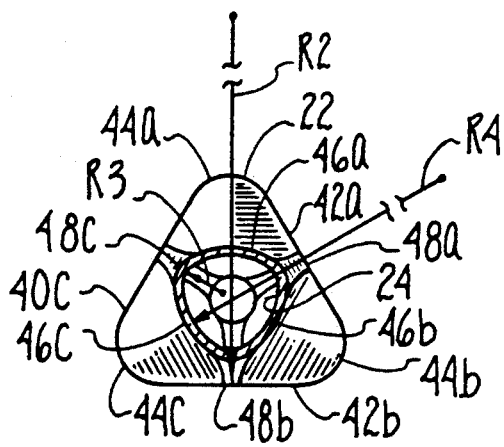
FIG. 4A is a cross-sectional view of the balloon as seen along the line 4—4 in FIG. 2.
Figure 4B:
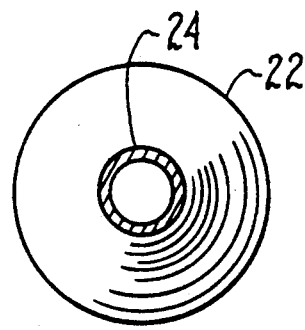
FIG. 4B is a cross-sectional view of the balloon with the balloon in its fully inflated configuration as would be seen along the line 4—4 in FIG. 2.
Figure 4C:
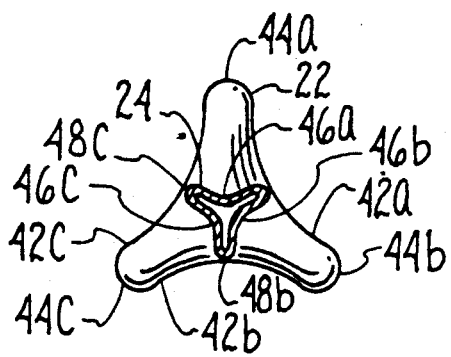
FIG. 4C is a cross-sectional view of the balloon with the balloon in the collapsed configuration, as would be seen along the line 4—4 in FIG. 2.

The details of balloon 10 can best be seen with cross-reference to FIGS. 4A, 4B and 4C. Specifically, FIG. 4A shows balloon 10 in its unstressed configuration, FIG. 4B shown balloon 10 in its inflated configuration, and FIG. 4C shows balloon 10 in its collapsed configuration. It can be seen in FIG. 4A that body portion 22 has three essentially flat folding regions 42a, b, c and three radially curved reinforcing regions 44a, b, c when balloon 10 is in its unstressed configuration. As can be appreciated in cross-reference to FIGS. 2, 3, and 4A, each of the folding regions 42a–c and reinforcing regions 44a–c extends longitudinally the length of body portion 22. Also, as shown, body portion 22 is formed with the folding regions 42a–c alternating with the reinforcing regions 44a–c. Stated differently, a reinforcing region 44 is formed on body portion 22 between successive folding regions 42.

Figure 5:
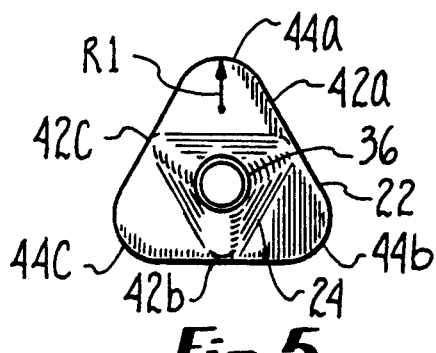
FIG. 5 is an end view of the balloon as seen along the line 5—5 in FIG. 2.

As best seen in reference to FIG. 5, each of the reinforcing regions 44a–c has a first radius of curvature R1 when balloon 10 is in its unstressed configuration. On the other hand, as best seen in FIG. 4A, each of the folding regions 42a–c has a second radius of curvature R2 which is greater than R1. In the preferred embodiment, each folding region 42a–c is flat, so that R2 is very large, i.e. R2 approaches infinity. Thus, the radius of curvature R2 of each folding region 42a–c, when balloon 10 is in the unstressed configuration shown in FIGS. 2, 3, and 4A, is greater than the radius of curvature R1 of each of the reinforcing regions 44a–c. Consequently, the folding regions 42a–c are relatively less stiff than are the reinforcing regions 44a–c.

Referring back to FIGS. 2 and 4A, each of the end portions 24, 26 is shown to include three connecting regions and three guiding regions. For clarity of disclosure, only the structure of end portion 24 will be discussed. It is to be understood, however, that the construction of end portion 26 is in all essential respects identical to the construction of end portion 24. As shown in cross-reference to FIGS. 2, 3, and 4A, end portion 24 has three connecting regions 46a–c which are radially separated by guiding regions 48a–c. Each of the connecting regions 46a–c and guiding region 48a–c, extends the length of end portion 24 and each guiding region 48 is formed on end portion 24 between successive connecting regions 46.

As best seen in reference to FIG. 4A, each of the guiding regions 48a–c defines a radius of curvature R3 when balloon 10 is in the unstressed configuration. On the other hand, as best seen in FIG. 4C, each of the connecting regions 46a–c is formed with a radius of curvature R4. In the preferred embodiment, each of the connecting regions 46a–c is essentially flat when balloon 10 is in the unstressed configuration, so that R4 approaches infinity. Thus, R4 is greater than R3, and the guiding regions 48a–c are consequently stiffer than the connecting regions 46a–c.

Importantly, as best shown in cross reference to FIGS. 2, 3, and 4A, each guiding region 48a–c of end portion 24 extends longitudinally from a folding region 42 of body portion 22. Also, each connecting region 46a–c of end portion 24 extends longitudinally from a reinforcing region 44 of body 22. More particularly, guiding region 48a of end portion 24 extends longitudinally from folding region 42a of body portion 22, guiding region 48b extends longitudinally from folding region 42b, and guiding region 48c extends longitudinally from folding region 42c. Similarly, connecting region 46a of end portion 24 extends longitudinally from reinforcing region 44a of body 22, connecting region 46b extends longitudinally from reinforcing region 44b, and connecting region 46c extends longitudinally from reinforcing region 44c. As shown in FIG. 4A, each guiding region 48 of end portion 14 is radially offset approximately sixty (60°) degrees from adjacent reinforcing regions 44 of body 22.

It is to be further understood that the guiding regions of end portion 26 longitudinally extend from the folding regions of body 22, while the connecting regions of end portion 26 longitudinally extend from the reinforcing regions of body 22.

Figure 6:
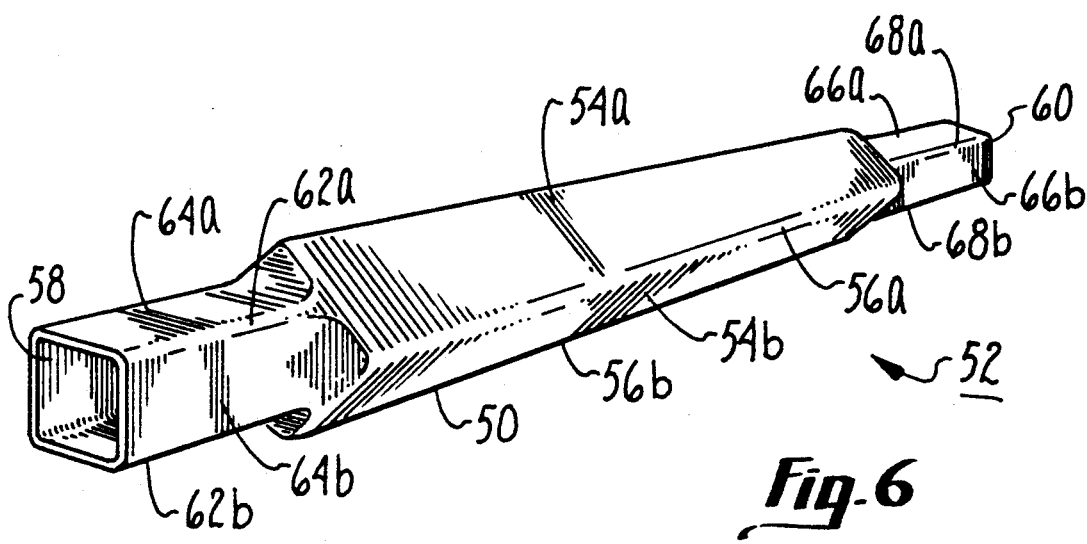
FIG. 6 is a perspective view of an alternate embodiment of the angioplasty balloon of the present invention.

While the balloon 10 described above has a body portion 22 that has three reinforcing regions and three folding regions, additional reinforcing regions and corresponding folding regions may be formed on balloon 10. For example, as shown in FIG. 6, a body portion 50 of a balloon 52 in accordance with the present invention could include four longitudinally-extending folding regions 54 (regions 54a, b shown in FIG. 6) separated by four longitudinally-extending reinforcing regions 56 (regions 56a, b shown in FIG. 6). As shown, end portion 58 would then also include four guiding regions 62 (regions 62a, b shown) and four connecting regions 64 (regions 64a, b shown). Each of the guiding regions 62 of end portion 58 would extend longitudinally from a corresponding folding region of body portion 50, while each connecting region 64 of end portion 58 would extend longitudinally from a corresponding reinforcing region 56 of body portion 50. It is to be understood that end portion 60 has four connecting regions 66 (regions 66a, b shown) and four guiding regions 68 (regions 68a, b shown). If desired, even more reinforcing and folding regions can be formed on balloon 10, in accordance with the above principles.

OPERATION

In the operation of balloon 10, reference is first made to FIG. 1. The interior of balloon 10 is first evacuated, to deflate balloon 10 to its collapsed configuration shown in FIGS. 1 and 4c. As shown, the relatively stiff curved guiding regions 48a–c of end portions 24, 26 (portion 26 not shown in FIG. 4C) guide the relatively less stiff folding regions 42a–c of body portion 22 into the pleated, minimum-area, radially compact cross sectional configuration shown in FIG. 4C.

Once balloon 10 is placed in its collapsed configuration, balloon 10 (and catheter 18) can be steered through catheter 21 until balloon 10 is positioned adjacent stenosis 16. Then, catheter 21 can be removed from patient 14, and fluid from source 20 can be infused into balloon 10 through catheter 18 in accordance with appropriate angioplasty procedures.

Balloon 10 is inflated until it is in its fully inflated configuration, shown in FIG. 4B. As shown, both body portion 22 and end portion 24 have substantially circular-shaped cross sections which are radially symmetrical when balloon 10 is fully inflated.

When in the fully inflated configuration shown in FIG. 4B, balloon 10 urges against the stenosis 16 to be relieved to compact or break up the stenosis. Then, fluid is withdrawn from balloon 10 to place balloon 10 in its unstressed configuration, shown in FIG. 4A. Further, additional fluid is withdrawn from balloon 10, i.e., balloon 10 is evacuated, to place balloon 10 in its collapsed configuration, shown in FIG. 4C. As balloon 10 is evacuated, fluid pressure outside of balloon 10 exceeds fluid pressure within balloon 10. Consequently, the substantially flat folding regions 42a–c of body portion 22 tend to collapse inwardly toward the axis of balloon 10, while the relatively stiffer curved reinforcing regions 44a–c tend to retain their general shape. As balloon 10 is evacuated, the relatively stiff curved guiding regions 48a-c of end portion 24 guide folding regions 42a-c of body portion 22 into a pleated, radially compact cross-sectional configuration. Balloon 10 may subsequently be removed from the patient's artery 12 through insertion catheter 21.

While the particular collapsible folding angioplasty balloon as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An angioplasty balloon formed in an unstressed configuration for inflation into an inflated configuration and deflation into a collapsed configuration, the balloon in its unstessed configuration comprising:

a body portion having a first end and a second end, said body portion in said unstressed configuration having a plurality of folding regions extending axially from said first end to said second end and defining a first radius of curvature, said body portion having a plurality of reinforcing regions defining a second radius of curvature less than said first radius of curvature with each said reinforcing region positioned between successive folding regions; and a first tapered end portion and a second tapered end portion, each of said end portions being integrally attached to a respective end of said body portion and each having a plurality of outwardly curved guiding regions, each said outwardly curved guiding region extending longitudinally from one of said folding regions of said body portion to guide said balloon into said collapsed configuration.

2. An angioplasty balloon as recited in claim 1 wherein said balloon has a substantially circular radial cross section defining a first radial cross-sectional area when said balloon is in said inflated configuration and a pleated cross section defining a second radial cross-sectional area smaller than said first area when said balloon is in said collapsed configuration.

3. An angioplasty balloon as recited in claim 1 wherein each of said outwardly curved guiding regions defines a third radius of curvature and each of said end portions further comprises a plurality of connecting regions, each said connecting region defining a forth radius of curvature greater than said third radius of curvature and each said connecting region extending longitudinally from one of said reinforcing regions of said body portion.

4. An angioplasty balloon as recited in claim 1 wherein said balloon is made of polyethylene terephthalate.

5. An angioplasty balloon as recited in claim 1 wherein balloon is made of polyetherimid.

6. An angioplasty balloon as recited in claim 1 wherein said balloon has three of said folding regions.

7. A collapsible angioplasty balloon, which comprises:

a hollow body portion formed in an unstressed configuration for inflation into an expanded configuration and deflation into a collapsed configuration, said body portion in said unstressed configuration having a first end and a second end and a plurality of folding regions and reinforcing regions extending longitudinally between said ends, each said reinforcing region being positioned between successive said folding regions; and first and second end portions having a plurality of connecting regions each extending longitudinally along said end portion from one of said reinforcing regions of said body portion and a plurality of outwardly curved guiding regions each extending longitudinally along said end portion from one of said folding regions of said body portion.

8. An angioplasty balloon as recited in claim 7 wherein said connecting regions of said end portions and said folding regions of said body portion define a first radius of curvature when said balloon is in said unstressed configuration, and said guiding regions of said end portions and said reinforcing regions of said body portion define a second radius of curvature when said balloon is in said unstressed configuration, said first radius of curvature being greater than said second radius of curvature.

9. An angioplasty balloon as recited in claim 8 wherein said balloon has a substantially circular radial cross section when said balloon is in said inflated configuration and a substantially pleated radial cross sectional shape when said balloon is in said collapsed configuration.

10. An angioplasty balloon as recited in claim 7 wherein said balloon is made of polyethylene terephthalate.

11. An angioplasty balloon as recited in claim 7 wherein balloon is made of polyetherimid.

12. An angioplasty balloon as recited in claim 7 wherein said balloon has three of said folding regions.

13. A collapsible angioplasty balloon, which comprises:

an elongated, hollow body portion defining a longitudinal axis and having a first end and a second end, said body portion having a plurality of folding regions and a plurality of reinforcing regions each extending longitudinally along said body portion, each said folding region being radially separated from adjacent said folding regions by one of said reinforcing regions; and a first end portion and a second end portion, each of said end portions having a widened base end integrally connected to one of said ends of said body portion and a narrow base end distanced from said body portion, said end portions being configured to collapse said folding regions of said body portion about said axis, said end portions further comprising a plurality of connecting regions and a plurality of outwardly curved guiding regions extending longitudinally therealong, each of said connecting portions being separated from adjacent connecting portions by one of said guiding portions.

14. An angioplasty balloon as recited in claim 13 wherein said end portions and said body portions are joined together with said connecting regions of said end portions extending longitudinally from said reinforcing regions of said body portion, and said guiding regions of said end portions extending longitudinally from said folding regions of said body portion.

15. An angioplasty balloon as recited in claim 14 wherein said balloon has a substantially circular radial cross section when said balloon is in said inflated configuration and a substantially pleated radial cross section when said balloon is in said collapsed configuration.

16. An angioplasty balloon as recited in claim 15 wherein said reinforcing regions and said guiding regions define a first radius of curvature when said balloon is in said collapsed configuration and said folding regions and said connecting regions define a second radius of curvature when said balloon is in said collapsed configuration, said first radius of curvature being smaller than said second radius of curvature for increased structural stiffness in said reinforcing regions and said guiding regions.

* * * * *